United States Patent
Buckwalter et al.

(10) Patent No.: US 8,522,310 B1
(45) Date of Patent: Aug. 27, 2013

(54) PSYCHOMETRIC KEYCARD FOR ONLINE APPLICATIONS

(75) Inventors: John Galen Buckwalter, Sierra Madre, CA (US); Kabir Sagoo, Granada Hills, CA (US)

(73) Assignee: TidePool, Inc., San Francisco, CA (US)

( * ) Notice: Subject to any disclaimer, the term of this patent is extended or adjusted under 35 U.S.C. 154(b) by 0 days.

(21) Appl. No.: 13/344,440

(22) Filed: Jan. 5, 2012

(51) Int. Cl.
*H04L 9/32* (2006.01)

(52) U.S. Cl.
USPC ........................................ 726/2; 726/3; 726/4

(58) Field of Classification Search
USPC .................. 726/2–10, 26–30; 713/168–170, 713/172, 186, 189, 192–194
See application file for complete search history.

(56) References Cited

U.S. PATENT DOCUMENTS 5,821,871 A * 10/1998 Benzler ........................... 340/5.8
7,836,492 B2 * 11/2010 Srinivasan et al. ................. 726/6

OTHER PUBLICATIONS

Vanessa Zainzinger, They know what you like—Cognitive Match teams up for real-time targeted advertising, Oct. 26, 2011.

* cited by examiner

*Primary Examiner* — Hosuk Song
(74) *Attorney, Agent, or Firm* — Van Pelt, Yi & James LLP

(57) ABSTRACT

A system for securely providing psychometric information is disclosed. The system includes a psychometric information database storing the psychometric information, wherein the psychometric information corresponds to an individual, and wherein the psychometric information is derived from an interaction with the individual. The system includes a validation module configured to validate an entity requesting the psychometric information. The system further includes an authorization module configured to selectively allow usage of a portion of the psychometric information based at least in part on a type of the portion of the psychometric information and at least in part on the interaction from which the portion of the psychometric information was derived.

32 Claims, 3 Drawing Sheets

PSYCHOMETRIC KEYCARD FOR ONLINE APPLICATIONS

BACKGROUND OF THE INVENTION

An application, e.g., an online application or a mobile application, can be individualized based on information specific to a user. However, existing techniques only utilize a limited amount and limited types of information corresponding to the user for this purpose. Therefore, improved techniques for securely providing information corresponding to an individual to an application so as to enable the application to provide individualized services would be desirable.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
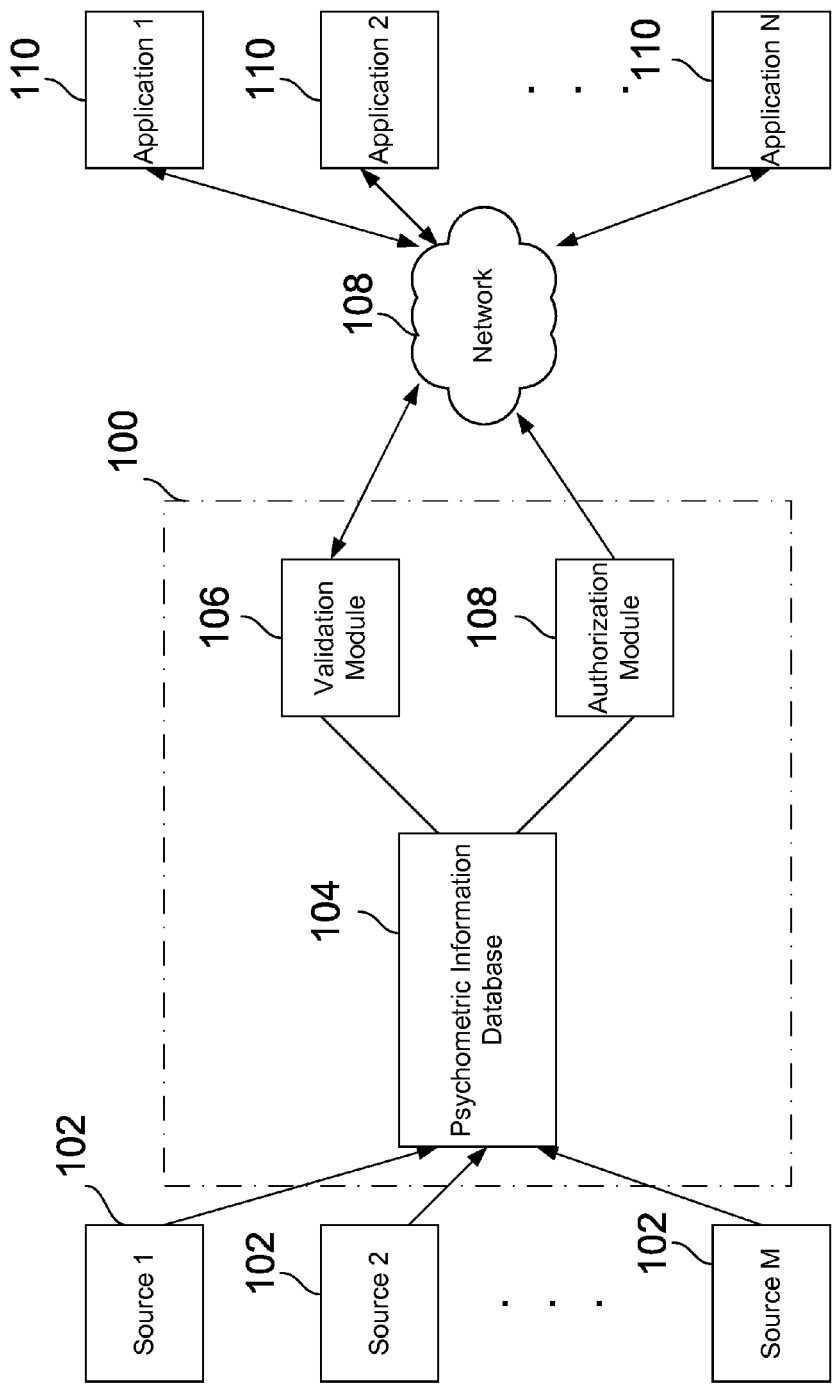
FIG. 1 is a block diagram illustrating an embodiment of a psychometric keycard system 100 for securely providing psychometric information of an individual to an application, e.g., an online application or a mobile application.

FIG. 1 is a block diagram illustrating an embodiment of a psychometric keycard system 100 for securely providing psychometric information of an individual to an application, e.g., an online application or a mobile application. Psychometric keycard system 100 includes a psychometric information database 104 for storing psychometric information of different individuals. For example, the psychometric information stored in psychometric information database 104 may include one or more characteristics associated with an individual, including characteristics related to personality, personal values, and the like. The psychometric information may also include other analyzed results that are derived from one or more characteristics associated with the individual. For example, the individual may be ranked or evaluated based on different characteristics associated with the individual, and the ranks or scores are stored in psychometric information database 104.

As shown in FIG. 1, the psychometric information may be received from different sources 102. For example, one of the sources is a computer game that presents one or more game scenarios to an individual. The responses of the individual to the one or more game scenarios are collected and analyzed by the computer game for evaluating the individual based on one or more characteristics. The collected responses and analyzed results are then stored into psychometric information database 104. In another example, one of the sources is a psychometric test, such as the Myers-Briggs Type Indicator (MBTI) assessment, which is a psychometric questionnaire designed to measure how people perceive the world and make decisions.

With continued reference to FIG. 1, psychometric keycard system 100 may provide psychometric information of an individual to different types of applications 110. For example, a search engine may use the psychometric information of a user to provide search results that are more relevant or useful to the user. In another example, an online retailer may use the psychometric information of an online shopper to select advertisements that may be of greater interest to the online shopper, thus achieving higher overall click-through rates within the online retailer site. In some embodiments, an application contacts psychometric keycard system 100 requesting for psychometric information corresponding to an individual to be used by the application. The request is then processed by a validation module 106, which validates the request based on different criteria. For example, the request is validated based on the type of the application, the identity of the entity hosting the application, configuration parameters set up by the individual, and the like. After the request is validated by validation module 106, an authorization module 108 in psychometric keycard system 100 then selectively allows usage of or access to the requested psychometric information by the application based on different criteria, as will be described in greater detail below. The psychometric information accessible by the application is referred to as the psychometric keycard information of the individual, which can be used by the application for providing individualized services to the individual.

In some embodiments, the one or more characteristics stored in psychometric information database 104 are related to different dimensions of an individual. For example, some dimensions are core traits that remain largely unchanged throughout an individual's life. Some dimensions are based on learning experience, and are more likely to change based on the life experiences and events of the individual.

Some characteristics are related to the five core dimensions of personality, including openness, conscientiousness, extraversion, agreeableness, and neuroticism. For example, characteristics related to openness include imagination and insight. Characteristics related to conscientiousness include a high level of thoughtfulness, good impulse control, and goal-directed behavior. Characteristics related to extraversion include excitability, sociability, talkativeness, assertiveness, and a high degree of emotional expressiveness. Characteristics related to agreeableness include trust, altruism, kindness, affection, and other pro-social behaviors. Characteristics related to neuroticism include emotional instability, anxiety, moodiness, irritability, and sadness.

Some characteristics are related to the different dimensions of personal values, i.e., the desirable qualities, principles, or standards of an individual. Some of these dimensions include family goals, health, love, spirituality, generosity, altruism, leadership, knowledge, work mastery, creativity, aesthetics, stability, security, recognition, excitement, financial gain, independence, moral fulfillment, community, and time freedom.

Some characteristics are related to the different dimensions of intrinsic or extrinsic motivations. Some characteristics are related to the different dimensions of work-life balance, including work, home, health, spirituality, quality and breath of relationships, and outside interests. Some characteristics are related to the different dimensions of resiliency, including perseverance, self-reliance, equanimity, and the like. Some characteristics are related to the different dimensions of social intelligence, including situation awareness, presence, authenticity, clarity, empathy, and the like. Other characteristics reflect the preferred cognitive styles and abilities. For example, some characteristics reflect whether an individual learns better when presented with visual-spatial information or with verbal or auditory information. Other cognitive characteristics include attention, working memory, memory, executive functioning and intelligence quotient. Note that the various characteristics described above are provided for illustration purposes only; accordingly, the present application is not limited to the above characteristics only.

Figure 2:
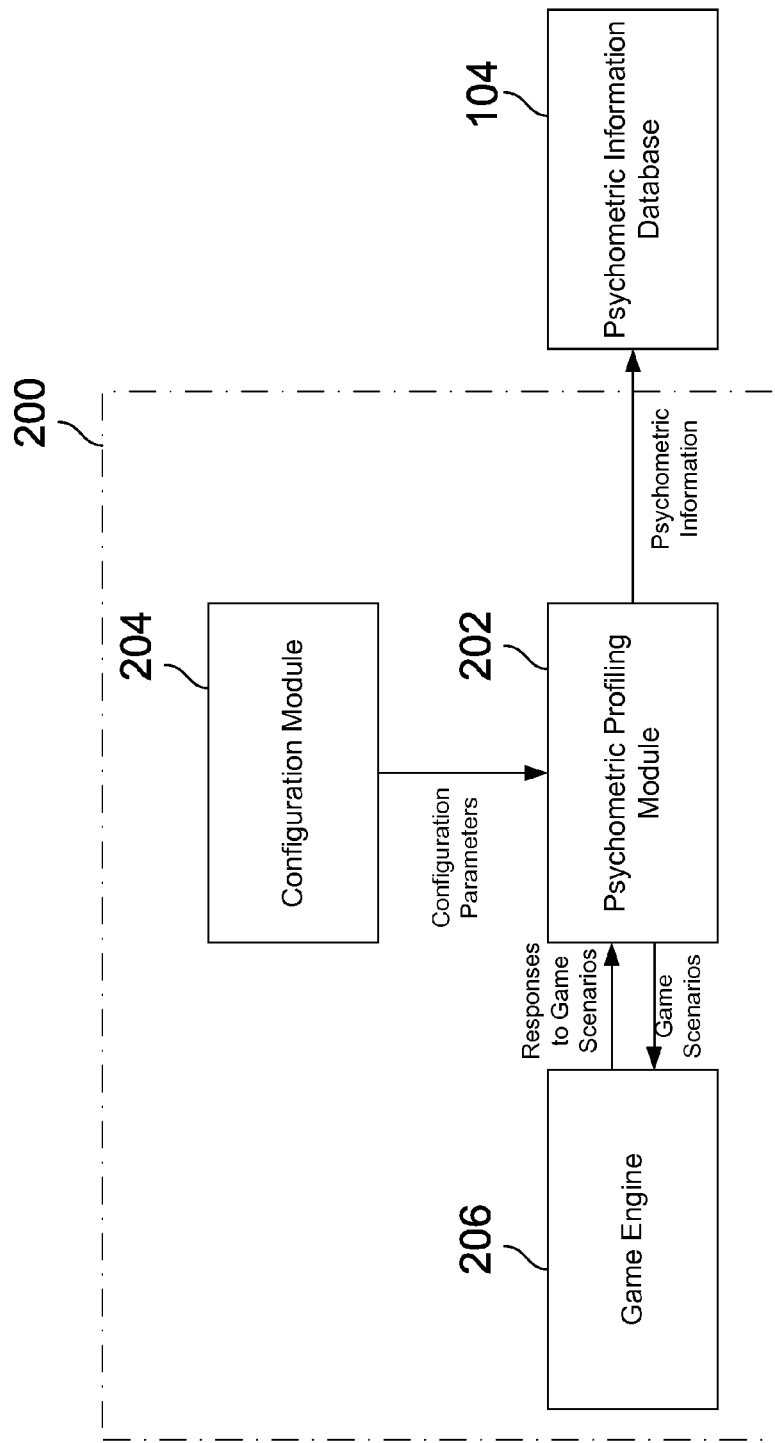
FIG. 2 is a block diagram illustrating an embodiment of a psychometric profiling computer game 200 for generating psychometric information corresponding to an individual.

The psychometric information stored in psychometric information database 104 may be received from different sources 102. FIG. 2 is a block diagram illustrating an embodiment of a psychometric profiling computer game 200 for generating psychometric information corresponding to an individual.

As shown in FIG. 2, psychometric profiling computer game 200 includes a psychometric profiling module 202. In some embodiments, psychometric profiling module 202 obtains one or more configuration parameters from a configuration module 204. The configuration parameters may be used to determine one or more characteristics associated with the individual to be evaluated by psychometric profiling computer game 200. Based on the one or more characteristics, psychometric profiling module 202 selects or dynamically generates one or more game scenarios to be presented to the individual by a game engine 206. The responses of the individual to the one or more game scenarios are collected and analyzed by psychometric profiling module 202 for evaluating the individual based on the one or more characteristics. The collected responses and analyzed results are then stored into psychometric information database 104.

Psychometric profiling module 202 may select from a game scenario repository or dynamically generate one or more game scenarios to be presented to the individual by game engine 206, and the individual plays the game (e.g., a video game or three-dimensional virtual reality game) by manipulating a mouse, joystick, the keys on the keyboard, or other input devices in response to the different game scenarios. In some embodiments, a particular game scenario may include graphical display, audio, or video sequences. In some embodiments, a game scenario includes a storyline with different characters and objects, and the individual plays the game by manipulating the different characters and objects to play out the storyline. In some embodiments, the storyline includes social interactions between the characters. In some embodiments, a game scenario presents to the individual different signals or stimuli, which will be described in greater detail below.

In some embodiments, the one or more game scenarios selected or dynamically generated by psychometric profiling module 202 to be presented to the individual by game engine 206 are selected or dynamically generated at least in part based on the one or more characteristics determined to be evaluated by psychometric profiling computer game 200. For example, in order to evaluate characteristics related to conscientiousness (e.g., thoughtfulness and impulse control), the selected or generated game scenario would put the individual in situations, e.g., lifelike situations, in which the individual is required to make decisions or take certain courses of actions that reflect the individual's level of conscientiousness.

For example, some decisions or courses of actions may reflect how organized or patient the individual is. Some decisions or courses of actions may reflect how motivated the individual is in achieving certain goals. And some decisions or courses of actions may reflect how motivated the individual is in pleasing or accommodating other people. Accordingly, as the individual makes decisions or takes certain courses of actions in response to different situations, the decisions or courses of actions of the individual may be collected, recorded, and analyzed for evaluating the characteristic that is currently being evaluated.

In some embodiments, the choices presented to the individual or the decisions that the individual are prompted to make are complex and multi-leveled. As a result, the individual may not be aware that her decisions are being evaluated based on a particular characteristic, thus reducing the chance that the individual may make choices or decisions that she believes will present herself in a better light to others.

The selected or generated game scenario may also display different icons, objects, or characters on the computer screen for the individual to click on or hover on using a mouse or other input devices. The level of interest that an individual has shown in certain objects, characters, or events may provide information regarding a characteristic associated with the individual. As the individual clicks on or hovers on different parts of the computer screen using a mouse or other input devices, a stream of these events (e.g., clickstream) can be collected, recorded, and analyzed for evaluating the characteristic that is currently being evaluated. For example, conscientiousness is positively associated with accepting responsibility and negatively associated with escape or avoidance. Therefore, the fact that an individual shows an interest in approaching problem-solving activities may be an indication that the individual has a relatively high level of conscientiousness.

In some embodiments, a game scenario presents to the individual different signals or stimuli, including colors, movements, velocity, how things are changed, text, and the like. Information about how the individual responds to these signals or stimuli can be used to evaluate different characteristics associated with the individual, as will be described in greater detail below.

In some embodiments, priming stimuli are included in a game scenario. Priming is the implicit memory effect in which exposure to a stimulus influences response to a later stimulus. Priming can occur following perceptual, semantic, or conceptual stimulus repetition. As an example, if a person reads a list of words including the word "table" and is later asked to complete a word starting with "tab," the probability that he will answer "table" is greater than if he is not so primed.

In another example, if a person sees a sequence of objects in a particular color, e.g., green, and is later asked to select one object from a few objects in different colors, the probability that he will select a green object is greater than if he is not so primed. Some people are more susceptible and responsive to certain types of priming stimuli than others. For example, the probability that the person will select a green object is greater if the person is more susceptible to visual priming stimuli than others.

People who are more prone to be primed or more easily influenced by a particular type of priming stimuli (e.g., colors) may share similar characteristics. Therefore, machine-learning techniques or other pattern recognition techniques may be employed offline or beforehand to identify the similar characteristics shared by those people who are more susceptible to the particular type of priming stimuli. When this particular type of priming stimuli is presented to an individual in a game scenario, information of how the individual is influenced by the priming stimuli can then be used to evaluate the identified characteristics associated with the individual.

As an illustrative example, a particular color, e.g., green, may be displayed one or more times as a visual priming stimulus in a game scenario. The individual is prompted by game engine 206 to select a subset of a few objects in different colors both before and after priming. If the individual selects more objects in the color green than objects in other colors after priming, then the individual may be assessed as someone who is more susceptible to the visual priming stimulus. Furthermore, if people who are susceptible to visual priming stimuli are found to be positively associated with (or correlated to) a particular characteristic (for example, characteristic1), then the individual may be evaluated by psychometric profiling computer game 200 as having a high level of characteristic1.

In some embodiments, the types of priming stimuli that are included in a game scenario may include visual priming stimuli (e.g., colors and shapes) and auditory priming stimuli. For example, a particular shape such as a circle may be displayed one or more times as a visual priming stimulus in a game scenario. In yet another example, a tune may be played one or more times as an auditory priming stimulus in a game scenario.

Information of how the individual is influenced by different types of priming stimuli can be useful in different applications. In some embodiments, this information may be useful for advertising or designing a corporate web portal. For example, if an individual has been evaluated by psychometric profiling computer game 200 as more susceptible to priming with objects in green colors, then when the individual is logged onto a corporate web portal or online website, the web portal or online website may display more of the text, icons, objects, and the like in different shades of green. This may increase the click-through rate of the website or the corporate web portal.

In some embodiments, sub-threshold (or subliminal) stimuli are included in a game scenario. Sub-threshold stimuli are any sensory stimuli that are below an individual's absolute threshold for conscious perception. The individual is not aware that sub-threshold stimuli have been presented to him/her. Sub-threshold stimuli include attractive faces, money, fast cars, and the like.

People who are more prone to be affected by a particular type of sub-threshold stimuli (e.g., money) may share similar characteristics. Therefore, machine-learning techniques or other pattern recognition techniques including linear and non-linear regression models may be employed offline or beforehand to identify the similar characteristics shared by those people who are more susceptible or responsive to a particular type of sub-threshold stimuli. When this particular type of sub-threshold stimuli is presented to an individual in a game scenario, information about how the individual is influenced by the sub-threshold stimuli can then be used to evaluate the identified characteristics associated with the individual.

As an illustrative example, a particular sub-threshold stimulus may be displayed one or more times in a game scenario. The individual is prompted by game engine 206 to make decisions in lifelike situations both before and after the individual is presented with the sub-threshold stimulus. If the decisions made by the individual reflect that the individual's certain characteristics, e.g., those related to personal values, are different before and after the sub-threshold stimulus is introduced, then the individual may be assessed as one who is more susceptible to the sub-threshold stimulus. Furthermore, if people who are more susceptible to a particular sub-threshold stimulus are found to be positively associated with characteristic2, then the individual may be evaluated by psychometric profiling computer game 200 as having a relatively high level of characteristic2.

In some embodiments, projective ambiguous stimuli are included in a game scenario. People respond differently to ambiguous stimuli, and this difference may provide important data on psychological characteristics. For example, suppose a person is shown a portion of a scenario with many colors on it and asked to describe the portion of that scenario. If he avoids talking about the different colors and describes the scenario as if it were in black and white or focuses on idiosyncratic features of the portion of that scenario, then the person may be assessed as being depressive or having some other relevant trait.

Therefore, machine-learning techniques or other pattern recognition techniques may be employed offline or beforehand to identify the similar characteristics shared by those people who are more prone to avoid a particular type of projective ambiguous stimuli. When a particular type of projective ambiguous stimuli is presented to an individual in a game scenario, information about how the individual is influenced by the projective ambiguous stimuli can then be used to evaluate the identified characteristics associated with the individual.

In some embodiments, psychometric profiling module 202 uses a current assessment of the individual to select or dynamically generate subsequent game scenarios to be presented to the individual by game engine 206, so as to further confirm or fine tune the current assessment. In some embodiments, a game scenario includes a plurality of variable components or a plurality of test variables. For example, different components or different test variables within a game scenario may be used to present different stimuli and put the individual in different lifelike situations for evaluating the different characteristics associated with the individual. These variable components or test variables may be selected based on a current assessment of the characteristics associated with the individual as well.

For example, if a current assessment of the individual indicates that the individual has a relatively high level of conscientiousness, then psychometric profiling module 202 may further confirm this assessment by selecting additional game scenarios or variable components within a game scenario that further evaluate the individual's level of conscientiousness. Psychometric profiling module 202 may also fine tune the assessment by evaluating different aspects of conscientiousness.

For illustration purposes, two exemplary game scenarios are disclosed herein. The first game scenario is for designing an avatar representing the individual in the game environment. In the second game scenario, the avatar representing the individual is placed in a carnival scene. Note that these two scenarios are provided for illustration purposes only; accordingly, the present application is not limited to these two specific scenarios only.

Some embodiments include a game scenario for designing an avatar representing the individual in the game environment. In this game scenario, the individual is prompted to design an avatar, including the avatar's skin color, sex, hair style, hair color, clothing, accessories, and the like. For example, the avatar may wear one or more of the following: a suit, shirt with shorts, shirt with jeans, and accessories including glasses, sunglasses, hats, and tattoos. In some embodiments, the selection process by the individual is recorded. For example, information about how long the individual takes to make certain selections and the order in which the selections are made can be recorded. This collected information can be used to evaluate how the individual views himself, which can be used as an initial assessment for the individual.

Some embodiments include a game scenario in which the avatar representing the individual is placed in a castle carnival scene. In order to breach a castle wall and reach the castle's inner keep where the villain is, the avatar is instructed that he must find, be given, or win five pages from a book. As the avatar approaches the castle, a bright carnival lies just outside the castle gates, and a dog wearing a bright green (priming with visual priming stimuli) hat carries one of the pages into the carnival. The best friend of the avatar says that there must be more pages within the carnival. He suggests to the avatar that he needs a disguise and points out a man in a green suit (priming with visual priming stimuli) standing outside the carnival who is selling masks that represent different emotions, such as happy, sad, or angry. Only one of these emotions matches an emotion that has previously been presented as a sub-threshold stimulus. The avatar is then asked to select a mask. If the avatar selects the mask with an emotion matching that which has previously been presented as a sub-threshold stimulus, then the individual may be evaluated as more susceptible to the sub-threshold stimulus. After the avatar puts on the mask, the avatar and his best friend walk to the entrance of the carnival. A bouncer stops the avatar and says that he needs a ticket to enter the carnival. The bouncer says that the avatar and his best friend may either look through the trash for a ticket or ask a group of masked carnival goers. The approach that the avatar chooses to take can be used to evaluate the individual's level of conscientiousness, including his level of approach/avoidance motivation, organization and desire for achievement.

With continued reference to FIG. 1, besides computer games, other sources 102 may be used to feed psychometric information into psychometric keycard system 100. For example, one of the sources is a psychometric test, such as the Myers-Briggs Type Indicator (MBTI) assessment, which is a psychometric questionnaire designed to measure how people perceive the world and make decisions. The purpose of the MBTI personality inventory is to use the theory of psychological types defined by C. G. Jung as the foundation for describing individuals' personalities. There are four dimensions of personality in the MBTI, each with two opposite preferences. These two preferences forming the four dimensions are extraversion/introversion, sensing/intuition, thinking/feeling and judging/perceiving. Everyone falls into one of 16 types formed by these dimensions. This type is purported to predict one's behavior in all situations. The MBTI is frequently used in team building, executive coaching, career counseling, professional development, marketing, leadership training, personal development, and marriage counseling.

The psychometric keycard can also store information associated with specific geolocations as determined by the coordinates of users' smartphones and other wireless devices. By accumulating psychometric data based on the influx of people who visit a specified geolocation, it is possible to use the psychometric information to build geolocation keycards. Thus if a restaurant is at a specific location the cumulative characteristic of users of this restaurant can be obtained through the geolocation keycard associated with the restaurant. This will allow for the recommendation of businesses (restaurants, stores, bars and the like) that are well-suited to the user's psychometric characteristics.

If there are digital advertising spaces available at specific geolocations where a user is located, e.g., a restaurant that uses iPads for menus or by a digital billboard or kiosk, user-specific advertising based on the user's psychometric characteristics can be delivered.

Geolocation of users will also allow for the development of services related to the transfer of psychometric information desired by both users, such as matching. For example, if the owner of a business who wishes to hire a person with a specific psychometric profile is attending a Lakers game at which a person with the desired profile is also in attendance, notifications between the two users could be made.

With continued reference to FIG. 1, psychometric keycard system 100 may provide psychometric information of an individual to different types of applications 110. For illustration purposes, a number of exemplary applications 110 are disclosed herein. Note that these exemplary applications 110 are provided for illustration purposes only; accordingly, the present patent application is not limited to the specific disclosed examples only.

In some embodiments, application 110 is a web search engine designed to search for information on the World Wide Web. The web search engine may use the various types of psychometric information that is available from psychometric information database 104 to provide search results that are more relevant or useful to a particular user. The web search engine may rank some of the search results corresponding to a specific search higher because those search results are more compatible with some of the user's psychometric characteristics that are relevant to the search. For example, the user's characteristics that are relevant to the search may include one or more of the following: characteristics that are related to any of the five core dimensions of personality, characteristics that are related to different dimensions of personal values, and characteristics that are related to different dimensions of intrinsic or extrinsic motivations.

For example, suppose a user enters a query into the web search engine to search for restaurants in the San Francisco Bay Area. With the psychometric keycard information of the user, the web search engine may match the user with restaurants based on the restaurants' decor or atmosphere, wait staff personality, restaurant patron personality, and the like. For example, a user who has extraverted characteristics may be matched with restaurants with wait staff that are more gregarious and sociable, whereas a user who has introverted characteristics may be matched with restaurants with wait staff that are more reserved and formal. In another example, a user who places a high personal value on aesthetics may be matched with restaurants that put a stronger focus on their decor or atmosphere, as opposed to other things, such as the quality of the food served.

Similarly, other applications 110 that may make use of the psychometric keycard information of users to match the users with services include movie rental websites (e.g., Netflix.com), online reservation websites (e.g. Hotels.com and Travelocity.com), social networking sites (e.g., Facebook, Twitter, and LinkedIn), online dating or friendship websites (e.g., Match.com), and the like.

In some embodiments, psychometric information is used to design a user interface for a machine, including a computer, a smart phone, a tablet computer, an interactive kiosk, and the like. In some embodiments, psychometric information is used to design a user interface for a computer program, including an internet browser. Different people have different cognitive learning styles. For example, some people are visual-spatial learners, and they prefer using images, pictures, colors, and maps to organize information and communicate with others, whereas some people are verbal and auditory learners, and they communicate better with text or speech. Different people also have different cognitive abilities. The level of attention to different types of information, the amount of working memory, the intelligence quotient (IQ) are also different from one person to another. Accordingly, a user interface can be designed such that the presentation style, the layout of the user interface, or the complexity of the information presented, is more conducive to effective processing of the information by the particular individual based on his/her cognitive characteristics, including cognitive abilities and learning styles. For example, a user interface may present information primarily with images or videos to a visual-spatial user, but present information primarily with text or audio clips to a verbal and auditory user. In another example, the complexity or the depth of the information presented by the user interface may be determined based on the amount of working memory or the estimated IQ of the user.

Similarly, other applications 100 that may make use of the cognitive characteristics included in the psychometric keycard information of users include news websites (e.g., CNN.com and NYTIMES.com), online dictionaries or encyclopedias (e.g., Dictionary.com and Wikipedia.com), and the like.

In some embodiments, application 110 is an advertising engine. An advertising engine may use the different types of characteristics included in the psychometric keycard information of a user to increase the click-through rate of the advertisements (e.g., web banners embedded in webpages) presented to the user. For example, the advertising engine may present more web banners related to health products (e.g., vitamins, herbal supplements, and fitness clubs) to a user who places a high personal value on physical or mental health. In another example, the advertising engine may utilize information regarding how a user responses to different signals or stimuli, including colors, shapes, sounds, movements, velocity, how things are changed, text, and the like, to design web banners with higher click-through rates by including preferred signals and stimuli. The different signals and stimuli that can be used include the various stimuli discussed previously in the present application, such as priming stimuli, sub-threshold stimuli, and projective stimuli. For example, if a user is more susceptible to priming with objects in green colors according to his/her psychometric keycard information, then when the user is logged onto an online website, the advertising engine may display more of the text, icons, objects, and the like in the web banner in different shades of green.

Applications 110 can access or use the psychometric keycard information of a user via different mechanisms. The mechanism used may be determined by the partnership between psychometric keycard system 100 and the entity hosting the application. In some embodiments, a user of an application 110 may access the application's website using a web browser. Once the user is on the application's website, an API or a browser plug-in may be launched to communicate with psychometric keycard system 100. Psychometric keycard system 100 may then prompt the user to enter his/her psychometric keycard user identification (ID) for authentication purposes. In some embodiments, a user may log into psychometric keycard system 100 first; the user may then access different applications 110 using his/her psychometric keycard such that individualized services, e.g., specific advertising, may be provided to the user.

With continued reference to FIG. 1, application 110 contacts psychometric keycard system 100 requesting psychometric keycard information corresponding to the user to be used as input into different decision processes of the application. In some embodiments, validation module 106 validates the request by application 110 based on different criteria. For example, the request is validated based on the type of the application, the identity of the entity hosting the application, configuration parameters (e.g., those related to user privacy) set up by the individual, and the like.

After the request is validated by validation module 106, authorization module 108 in psychometric keycard system 100 then selectively allows usage of or access to the requested psychometric information by application 110 based on different criteria. The subset of psychometric information that can be used or accessed by application 110 may be determined based on one or more of the following: the type of the application, the identity of the entity hosting the application, configuration parameters set up by the user, the source from which the psychometric information is derived, the type of the psychometric information requested, and the like. Suppose a user has taken a psychometric profiling computer game 200 administered by his company. The game may be designed for human resource management, team development, designing employee benefit packages, developing employee training programs, and the like. For privacy reasons, the user may configure his/her psychometric keycard account such that the psychometric information derived from this particular source cannot be used or accessed by applications unless they have obtained explicit approval by the user. In another example, a user may be paid to do an online consumer survey while the user is using an application; in this instance, all of his/her psychometric information stored in psychometric information database 104 may be made available to the application.

Once the subset of the psychometric information that can be used or accessed by a specific application 110 (i.e., the psychometric keycard information) is determined, the psychometric keycard information may be fed as input into different decision processes of the application. In some embodiments, the psychometric keycard information is sent to application 110 in an encrypted message. The message may include a number of fields, including psychometric characteristics, a reliability value associated with the characteristics, sources from which the psychometric characteristics are derived, levels of responsiveness to different stimuli, and the like. Reliability values are estimates of the consistency of a psychometric characteristic, for example how likely is it that the same individual will obtain a similar score on a specific psychometric characteristic were the individual to take the same psychometric profiling game on a second occasion. There are numerous reliability values including test-retest reliability, inter-method reliability and internal consistency reliability. The most commonly used internal consistency reliability value is Cronbach's alpha value. Cronbach's alpha is derived from the average of the intercorrelations between all items used to assess a psychometric characteristic. Thus it becomes larger as internal consistency increases. In general, values at or above 0.7 are considered acceptable, values less than 0.7 and at or above 0.5 are questionable, and values below 0.5 are unacceptable. In some embodiments, the psychometric keycard information is not sent to application 110; rather, the psychometric keycard information is used by psychometric keycard system 100 internally for making decisions on behalf of application 110. For example, in designing a web banner, an advertising engine may need to choose one of two different images to be displayed on the web banner. The advertising engine may send the two images to psychometric keycard system 100, and the system will use the psychometric keycard information associated with the user to select one of the images on behalf of the advertising engine.

Figure 3:
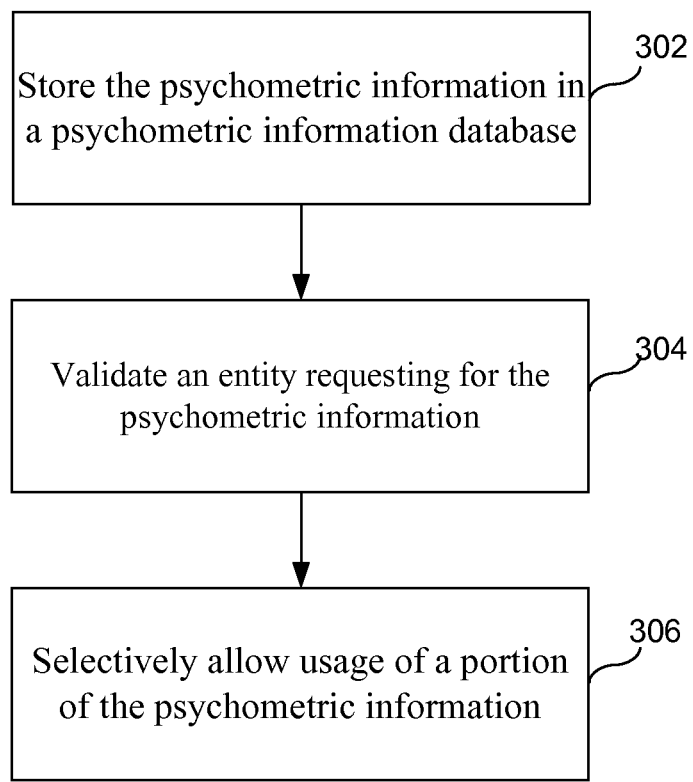
FIG. 3 is a diagram illustrating an embodiment of a process 300 for securely providing psychometric information of an individual.

FIG. 3 is a diagram illustrating an embodiment of a process 300 for securely providing psychometric information of an individual. In some embodiments, process 300 is a process for system 100 in FIG. 1.

At step 302, psychometric information of the individual is stored in a psychometric information database. The psychometric information is derived from an interaction with the individual. In some embodiments, the interaction with the individual includes a psychometric test, including the MBTI assessment and a psychometric profiling computer game. In some embodiments, the psychometric information includes a characteristic that is related to one or more of the following: personality, personal values, motivations, work-life balance, resiliency, social intelligence, and cognition. In some embodiments, the psychometric information includes a score or a rank that is based at least in part on one or more characteristics described above. In some embodiments, the psychometric information includes a reliability value that is associated with one of the characteristics described above. In some embodiments, the psychometric information includes information regarding the source of the psychometric information. In some embodiments, the psychometric information includes a level of responsiveness of the individual to one or more of the following: a priming stimulus, a sub-threshold stimulus, and a projective ambiguous stimulus.

At 304, an entity requesting psychometric information is validated. For example, the entity may be validated based on one or more of the following: the type of the psychometric information requested, the identity of the entity, and the configuration parameters set by the individual. In some embodiments, the entity is associated with an application, including a web search engine, a business or service application, a social networking application, and a relationship matching application. In some embodiments, the entity is associated with the designing of a user interface for the individual. The user interface may be an interface for a machine, including a computer, a smart phone, a tablet computer, an interactive kiosk, and the like. The user interface may be an interface for a computer program, including a browser and the like. In some embodiments, the entity is associated with an advertising engine.

At 306, a portion of the psychometric information is selectively allowed to be used for one or more decision processes associated with the entity. In some embodiments, the portion of the psychometric information allowed to be used is determined by one or more of the following: the type of the information, the source of the information, the type of the application, the entity hosting the application, and configuration parameters.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for securely providing psychometric information, comprising:
   a psychometric information database storing the psychometric information, wherein the psychometric information corresponds to an individual, and wherein the psychometric information is derived from an interaction with the individual, wherein the interaction with the individual comprises a psychometric test, and wherein the psychometric test comprises a psychometric profiling computer game, and wherein the psychometric profiling computer game is configured to:
      present one or more game scenarios to the individual;
      collect responses of the individual to the one or more game scenarios; and
      evaluate one or more characteristics associated with the individual based at least in part on the collected responses of the individual;
   a validation module configured to validate an entity requesting the psychometric information; and
   an authorization module, using a processor to selectively allow usage of a portion of the psychometric information based at least in part on a type of the portion of the psychometric information and at least in part on the interaction from which the portion of the psychometric information was derived.

2. The system of claim 1, wherein the psychometric information comprises a characteristic related to one or more of the following: personality, personal values, motivations, work-life balance, resiliency, social intelligence, and cognition.

3. The system of claim 2, wherein the psychometric information further comprises a score or a rank based at least in part on the characteristic.

4. The system of claim 2, wherein the psychometric information further comprises a reliability value associated with the characteristic.

5. The system of claim 1, wherein the psychometric information comprises a portion of the interaction.

6. The system of claim 1, wherein the psychometric information comprises a level of responsiveness of the individual to one or more of the following: a priming stimulus, a sub-threshold stimulus, and a projective ambiguous stimulus.

7. The system of claim 1, wherein one of the one or more game scenarios includes a storyline that includes social interactions, and wherein the individual plays the game scenario by playing out the storyline as an avatar.

8. The system of claim 1, wherein the entity is associated with a web search engine, and wherein the web search engine uses the portion of the psychometric information to provide search results for a search based at least in part on the portion of the psychometric information.

9. The system of claim 8, wherein the search comprises a search for a business or a service.

10. The system of claim 1, wherein the entity is associated with a business or a service application, and wherein the application is an online or mobile application.

11. The system of claim 1, wherein the entity is associated with a social networking application.

12. The system of claim 1, wherein the entity is associated with a relationship matching application.

13. The system of claim 1, wherein the entity is associated with designing of a user interface for the individual.

14. The system of claim 13, wherein the designing of the user interface comprises using the portion of the psychometric information to determine one or more of the following: a presentation style, a layout of the user interface, and a complexity level presented by the user interface.

15. The system of claim 1, wherein the entity is associated with an advertising engine, and wherein the advertising engine uses the portion of the psychometric information to provide an advertisement targeted to the individual based at least in part on the portion of the psychometric information.

16. The system of claim 15, wherein providing the advertisement targeted to the individual based at least in part on the portion of the psychometric information comprises including a stimulus in the advertisement, and wherein the stimulus is one of the following: a priming stimulus, a sub-threshold stimulus, and a projective ambiguous stimulus.

17. The system of claim 1, wherein the validation of the entity is based at least in part on one or more of the following: a type of an application associated with the entity, an identity of the entity, and configuration parameters set by the individual.

18. The system of claim 1, wherein the authorization module is further configured to selectively allow usage of the portion of the psychometric information based at least in part on one or more of the following: a type of an application associated with the entity, an identity of the entity, an approval by the individual, and configuration parameters.

19. The system of claim 1, wherein the portion of the psychometric information is sent to the entity in an encrypted message.

20. The system of claim 1, further comprising a decision module configured to make a decision on behalf of the entity associated with an application, wherein the decision is based at least in part on the portion of the psychometric information.

21. A method for securely providing psychometric information, comprising:
   storing the psychometric information in a psychometric information database, wherein the psychometric information corresponds to an individual, and wherein the psychometric information is derived from an interaction with the individual, wherein the interaction with the individual comprises a psychometric test, and wherein the psychometric test comprises a psychometric profiling computer game, and wherein the psychometric profiling computer game is configured to:
      present one or more game scenarios to the individual;
      collect responses of the individual to the one or more game scenarios; and
      evaluate one or more characteristics associated with the individual based at least in part on the collected responses of the individual;
   validating an entity requesting the psychometric information using a processor; and
   selectively allowing usage of a portion of the psychometric information based at least in part on a type of the portion of the psychometric information and at least in part on the interaction from which the portion of the psychometric information was derived.

22. A computer program product for securely providing psychometric information, the computer program product being embodied in a non-transitory computer readable storage medium and comprising computer instructions for:
   storing the psychometric information in a psychometric information database, wherein the psychometric information corresponds to an individual, and wherein the psychometric information is derived from an interaction with the individual, wherein the interaction with the individual comprises a psychometric test, and wherein the psychometric test comprises a psychometric profiling computer game, and wherein the psychometric profiling computer game is configured to:
      present one or more game scenarios to the individual;
      collect responses of the individual to the one or more game scenarios; and
      evaluate one or more characteristics associated with the individual based at least in part on the collected responses of the individual;
   validating an entity requesting the psychometric information; and
   selectively allowing usage of a portion of the psychometric information based at least in part on a type of the portion of the psychometric information and at least in part on the interaction from which the portion of the psychometric information was derived.

23. A system for securely providing psychometric information, comprising:
   a psychometric information database storing the psychometric information, wherein the psychometric information corresponds to an individual, and wherein the psychometric information is derived from an interaction with the individual;
   a validation module configured to validate an entity requesting the psychometric information, wherein the entity is associated with an advertising engine; and
   an authorization module, using a processor to selectively allow usage of a portion of the psychometric information based at least in part on a type of the portion of the psychometric information and at least in part on the interaction from which the portion of the psychometric information was derived, and wherein the advertising engine uses the portion of the psychometric information to provide an advertisement targeted to the individual based at least in part on the portion of the psychometric information.

24. The system of claim 23, wherein the psychometric information comprises a characteristic related to one or more of the following: personality, personal values, motivations, work-life balance, resiliency, social intelligence, and cognition.

25. The system of claim 23, wherein the psychometric information comprises a portion of the interaction.

26. The system of claim 23, wherein the psychometric information comprises a level of responsiveness of the individual to one or more of the following: a priming stimulus, a sub-threshold stimulus, and a projective ambiguous stimulus.

27. The system of claim 23, wherein the interaction with the individual comprises a psychometric test.

28. The system of claim 27, wherein the psychometric test comprises a psychometric profiling computer game.

29. The system of claim 28, wherein the psychometric profiling computer game is configured to:
   present one or more game scenarios to the individual;
   collect responses of the individual to the one or more game scenarios; and
   evaluate one or more characteristics associated with the individual based at least in part on the collected responses of the individual.

30. The system of claim 29, wherein one of the one or more game scenarios includes a storyline that includes social interactions, and wherein the individual plays the game scenario by playing out the storyline as an avatar.

31. A method for securely providing psychometric information, comprising:
- storing the psychometric information in a psychometric information database, wherein the psychometric information corresponds to an individual, and wherein the psychometric information is derived from an interaction with the individual;
- validating an entity requesting the psychometric information using a processor, wherein the entity is associated with an advertising engine; and
- selectively allowing usage of a portion of the psychometric information based at least in part on a type of the portion of the psychometric information and at least in part on the interaction from which the portion of the psychometric information was derived, and wherein the advertising engine uses the portion of the psychometric information to provide an advertisement targeted to the individual based at least in part on the portion of the psychometric information.

32. A computer program product for securely providing psychometric information, the computer program product being embodied in a tangible non-transitory computer readable storage medium and comprising computer instructions for:
- storing the psychometric information in a psychometric information database, wherein the psychometric information corresponds to an individual, and wherein the psychometric information is derived from an interaction with the individual;
- validating an entity requesting the psychometric information using a processor, wherein the entity is associated with an advertising engine; and
- selectively allowing usage of a portion of the psychometric information based at least in part on a type of the portion of the psychometric information and at least in part on the interaction from which the portion of the psychometric information was derived, and wherein the advertising engine uses the portion of the psychometric information to provide an advertisement targeted to the individual based at least in part on the portion of the psychometric information.

* * * * *